United States Patent [19]

Quintern

[11] Patent Number: 5,371,004
[45] Date of Patent: Dec. 6, 1994

[54] BIOLOGICAL DETECTION OF RADIATION

[75] Inventor: Lothar Quintern, Bornheim, Germany

[73] Assignee: Deutsch Forschungsanstalt fur Luft-und Raumfahrt E.V., Cologne, Germany

[21] Appl. No.: 116,206

[22] Filed: Sep. 2, 1993

Related U.S. Application Data

[63] Continuation of Ser. No. 801,065, Dec. 3, 1991, abandoned.

[30] Foreign Application Priority Data

Dec. 6, 1990 [DE] Germany .............................. 4039002

[51] Int. Cl.$^5$ .......................... C12M 1/00; C12N 3/00; C12N 15/00; C12Q 1/02
[52] U.S. Cl. .................................. 435/29; 435/174; 435/839; 435/173.8
[58] Field of Search ...................... 435/4, 29, 173, 174, 435/839

[56] References Cited

PUBLICATIONS

Munataka Mutation Research 82 (1981) 263–268.
Tyrrell Phatachemistry & Photobiology 1978 vol. 27 pp. 571–579.
Witkin, Science, vol. 152, pp. 1345–1352 (1966).
Berger, D. S. 1976, The sunburning ultraviolet meter: design and performance, Photochemistry and Photobiology, 24:587–593.
Henriksen, K., et al., 1989, Measurements of solar U.V., visible and near I.R. irradiance at 78° N, Atmospheric Environment, 23:1573–1579.
Horneck, G., et al., 1984, Microorganisms in the space environment, Science, 225:226–228.
Munakata, N. 1981, Killing and mutagenic action of sunlight upon Bacillus subtillis spores: a dosimetric system, Mutation Research, 82:263–268.
Tyrrell, R. M., et al. 1978, Solar dosimetry with repair deficient bacterial spores: action spectra, photoproduct measurements and a comparison with other biological systems, Photochem. and Photobio., 27:571–579.
Wong, C. F., 1989, A new dosimeter for ultraviolet-B radiation, Photochemistry and Photobiology, 50:611–615.
Calkins, J., et al., 1979, Photochem. Photobiol. 30:733–738.
Tanaka, Y., et al., 1985, Biological Abstract 80: 76324; Rep. Natl. Food Res. Inst. 0:914.

*Primary Examiner*—Michael G. Wityshyn
*Assistant Examiner*—Jane A. Williams
*Attorney, Agent, or Firm*—Fish & Richardson

[57] ABSTRACT

The present invention relates to a method and a device for the biological detection of radiation by microorganisms in form of a microorganism coating provided on a sheet substrate, which microorganism coating is exposed, optionally after calibration by exposure to a defined radiation dose, to the radiation to be detected. The principle of evaluating the biologically weighted quantification of the radiation dose consists of photometrically determining the decrease in response to the radiation dose of the amount of synthetically formed products upon selectively staining the biosynthesis products.

9 Claims, 1 Drawing Sheet

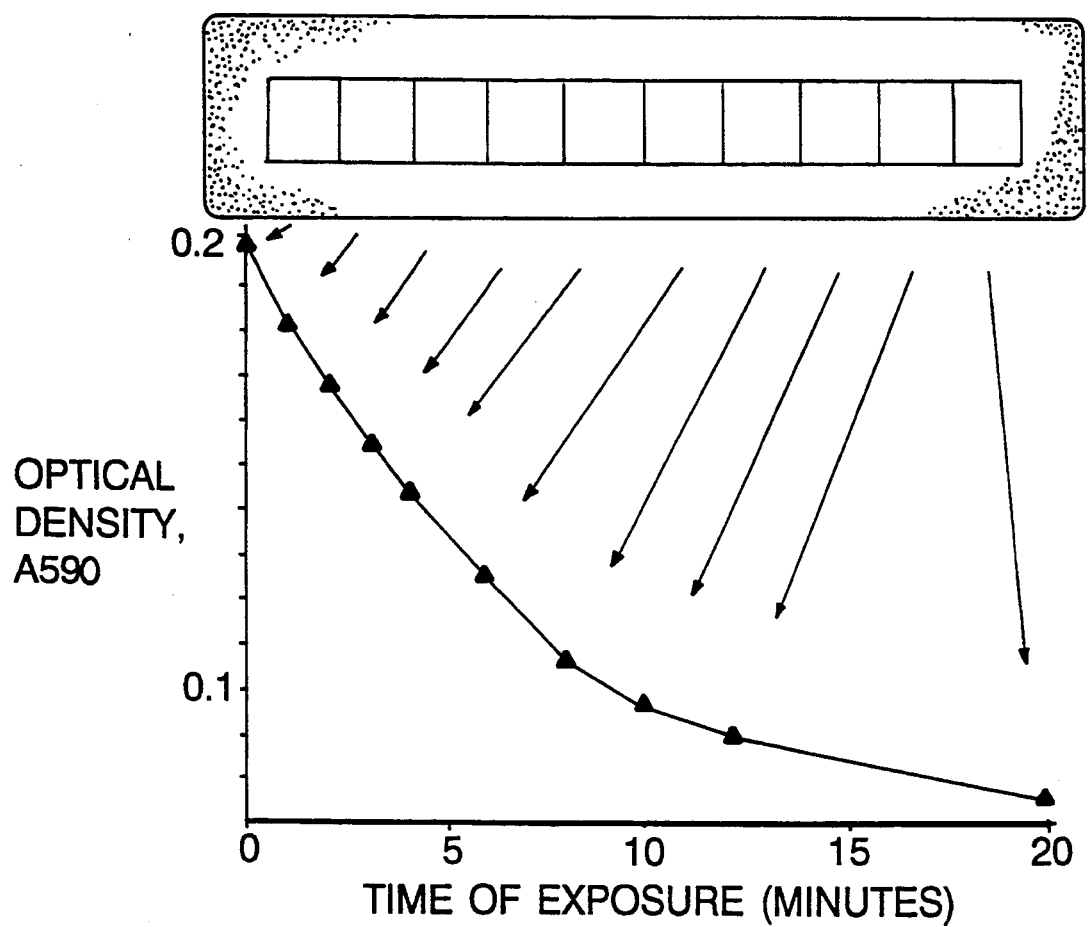
FIGURE

BIOLOGICAL DETECTION OF RADIATION

This is a continuation of application Ser. No. 07/801,065, filed Dec. 3, 1991, now abandoned.

The invention relates to a method and an apparatus for the biological detection of radiation by microorganisms, and especially for investigating the noxious effects to man and to the biosphere.

These demands require a detector which, in particular, exhibits a sensitivity curve largely corresponding to the erythema induction curve of man, allows a variable use, for example in global field measurements, and may be correctly operated by less skilled staff.

Various measuring concepts with biological weighting have been known from prior art, especially so relating to the UV-B dosimetry of terrestrial UV light.

Thus, D. S. Berger, in Photochemistry and Photobiology, 1976, Vol. 24, pp. 587–593, describes a measuring apparatus for the determination of UV radiation, wherein it is intended that the sensitivity of the detector be adapted to the spectrum of action for the induction of erythema in man. The fluorescence of a magnesium tungstate layer is quantified by using a combination of suitable filters. The described method suffers from the drawback of weighting in the application as a UV detector film. According to the method described therein, the short wave range of the UV-B spectrum is weighted too little, while the long-wave range is weighted too much. Thus, the UV-B variation as dependent on the ozone concentration is difficult to detect with this system.

C. F. Wong, R. Fleming and S. J. Carter, Photochemistry and Photobiology, 1989, Vol. 50, pp. 611–615, describe the exposure of sheets of plastic materials, the UV sensitivity of which is similar to the above-mentioned action spectrum followed by etching and photometric detection of the changed optical behavior of the sheet, e.g. of polycarbonate. Also this method attributes too little weight to the short-wave region of the UV-B spectrum and too much weight to the long-wave region. In the same manner, the UV-B variation in response to the ozone concentration is difficult to detect also with this system.

K. Henriksen, K. Stamnes and P. Østensen, Atmospheric Environment, 1989, Vol. 23, pp. 1573–1579, describe the wave length-resolving irradiance measurement of the terrestrial UV-A and UV-B radiation range. The resulting values could be balanced by means of suitable weighting factors. The very cost-intensive measurements require the use of an extensive combination of equipment, and more particularly an Ulbricht sphere covered by a quartz cupola, an automated motor-driven double monochromator, a photodetector, a photomultiplier including a high voltage source and the appropriate computer plus software.

R. M. Tyrrell, Photochemistry and Photobiology, 1978, Vol. 27, pp. 571–579, N. Munakata, Mutation Research, 82 (1981), pp. 263–268, and G. Herneck et al., Science, 1984, Vol. 225, pp. 226–228, describe biological UV dosimetry with microorganisms.

In this method, microorganisms in suspension or as a dried monolayer are exposed to UV radiation, and then the survival rate or the mutagenic activity is determined. In this method, the genetic material of the organisms (deoxyribonucleic acid polymer) is the Fain target for the UV radiation and, thus, results in a direct biological weighting of the received radiation dose. However, the measurement series described are very work-intensive with respect to the evaluation, so that the described methods hitherto have not been introduced in routine application technology.

In comparison to the above, it is the object of the present invention to combine the advantages of biological UV dosimetry using microorganisms with those of the inexpensive and simple methods mentioned.

This object is attained by a method for the biological detection of radiation by microorganisms, wherein (a) microorganisms are applied as a coating onto a sheet substrate, (b) selected first areas of the microorganism coating are optionally exposed to a defined dose of radiation, (c) said first areas optionally exposed to radiation are protected from the action of further incident radiation, (d) subsequently further selected second areas of the microorganism coating are exposed to the radiation to be detected, (e) the biosynthesis of the microorganisms is initiated in the optional first and the second areas of the microorganism coating upon termination of the exposure to radiation, and (f) the formation of products of the biosynthesis, and especially the cell inactivation and/or growth inhibition of the microorganisms, is photometrically determined in the optional first and the second areas of the microorganism coating.

The method according to the invention has the particular advantage of a direct biological weighting of the absorbed radiation, since mainly the genetic material serves as the target and, if damaged, leads to cell inactivation or growth inhibition. This is known to cause a lower protein formation in comparison to an unexposed microorganism.

The method according to the invention is extraordinarily economy-priced and is both simple to handle and to evaluate.

The method according to the invention can be realized in that a commercially available plastic substrate having a hydrophilic surface is employed onto which the biological grained material, for example spores of *Bacillus subtilis*, is applied. To this end, the microorganism may be applied onto the sheet at an elevated temperature in an aqueous carrier solution, and once the carrier solution has solidified, the resulting gel may be allowed to dry. The resulting sheet is well storage-stable in the dark for several months.

For a biological quantification, and especially for a weighted detection of, for example, the UV radiation in the sunlight, the microorganisms applied onto the substrate are exposed in suitable exposure containers outdoors, and preferably in a horizontal position. In the course thereof, calibration zones—if present—are kept dark and only selected areas of the substrate and of the microorganisms present thereon are exposed to the sunlight. In this exposure, neutral filters with vapor-deposited metal layers and/or edge-type filters may be employed, for example, in order to survey certain selected wave-length ranges or to adjust the desired periods of measurement. Usually the conditions of the irradiation are selected so that the effect is within a range as represented by a calibration curve.

Different dose-effect curves may be obtained, depending on the conditions of the incubation, so that it is preferred that the substrates are provided with calibration series. For this purpose, selected areas of the substrate and of the microorganisms coating are exposed to a defined radiation dose, preferably derived from an artificial radiation source having a known constant irradiance (sun simulator). The area thus exposed is then covered by a number of various neutral filters, the transmission of which may range, for example, from about 100% to 0.4%.

BRIEF DESCRIPTION OF THE DRAWING

In the Figure, there is shown a calibration series of an UV detector film, the individual segments of which were exposed to a source of radiation (simulated sunlight) for different periods of time.

Upon the completion of the exposure to radiation in the calibration zones and in the areas exposed to the radiation to be detected, biosynthesis by the microorganism coating is initiated. The film is then incubated, dyed, and the optical density of the dye is determined. The reported exposure times are calculated by using the transmission values of the employed neutral and/or edge filters.

Thus, the fundamental principle of the method according to the invention consists of an immobilization of the microorganisms, if so desired in a carrier, on a substrate. Thus, it is as well possible to bind the microorganisms to the substrate by means of a suitable chemical or adsorptive bond, for example as a monolayer.

The evaluation principle consists of quantifying the decrease dependent on the radiation dose of the products of the biosynthesis. Hereto, the substrate and the microorganism coating applied thereonto is incubated in a sterile nutrient medium for bacteria at a suitable temperature for a pre-determined period of time. Thereupon, surviving spores will germinate and grow to form microcolonies of, for example, from 10 to 100 monocellular organisms. The protein formed in the course thereof may be selectively dyed by using known staining and de-staining methods. After washing, for example with pure methanol, the microorganism coating is once more dried, and the absorbance thereof is determined at the absorption maximum of the highest wavelength of the dye employed. Then, areas exhibiting high absorbance values (high amounts of protein) correspond to lower UV doses, whereas low absorbance areas (low amounts of protein) correspond to areas exposed to high UV doses. The resulting absorbance values of the respective areas of exposure can now be compared to the values of the calibration series. As the relative biologically active UV dosage unit there may be defined, for example, that period of action which is achieved after an exposure for one minute to the calibrating light source. If the method according to the invention for the biological detection of radiation by means of microorganisms will be employed in a standardized procedure, then of course it will not be necessary that each individual specimen is calibrated, so that the required evaluation only consists of treating the microorganism coating after exposure under standardized conditions of incubation and also of carrying out the steps of staining and measuring the absorbance under well-defined conditions. Thus, in contrast to the evaluation procedures of the biological methods of the detection of radiation as sc far known in the state of the art, the method according to the invention constitutes a significant simplification.

According to the invention it is advantageous that a uniform spore density per unit area of the substrate is obtained by applying the microorganism in the form of a gel. More particularly, agarose gel adheres very well to plastic sheets, and especially to polyester sheets having hydrophilic surfaces. The coating remains adhered to the substrate sheet in all of the further process steps (incubation, staining, de-staining, drying and evaluation). Embedding the microorganisms into the agarose gel ensures a good fixation to the substrate sheet and a high survival rate of the unexposed spores to be obtained, so that the sheet will be storable for months. In the case of the detection of UV radiation, the UV-transparent agarose matrix ensures a good germination of the spores and a good growth to form suitable microcolonies. Staining the biosynthesis products on the sheet goes without complication. The measurement of the effect produced by the radiation (dose determination) is possible immediately on the sheet by way of an easy photometrical determination of the remission at a predetermined absorption maximum of the employed dye, usually the highest wave length absorption maximum. By employing a combined measurement array using various edge-type filters, it is possible to produce areas of controlled sensitivities in the UV-A, UV-A plus UV-B, and UV-A through UV-C ranges. Any dosage-rate dependence within the ranges of variation of terrestric UV intensities could not be observed.

The method according to the invention is adapted to observe an additive effect of the radiation doses. Even after different periods of storage, it could be verified that the sensitivity to UV radiation of the sheet had remained constant. The sensitivity to radiation only to an extremely low degree depends on the angle of incidence, so that this factor usually can be neglected. Also the temperature virtually does not exert any influence on the sensitivity to UV radiation. Humidity should be kept at a constant level during irradiation, if possible.

In a particularly preferred embodiment, the method according to the invention is distinguished in that the wave length range to be detected is selected by using edge-type filters. Thus, more particularly, the method according to the invention can be utilized for detecting UV radiation, and especially in the UV-A, -B and -C ranges. In the same manner, dosimetry is possible in the range of X-rays.

The manner of how to apply the microorganism coating onto the sheet substrate is not critical within the scope of the present invention. It is particularly preferred that the microorganism coating is applied onto the substrate as a suspension of the microorganism, followed by drying.

The direct biological weighting and dosimetry of the absorbed radiation can preferably be determined by measuring the amount of products formed by bioynthesis in the areas exposed to the radiation.

A particularly preferred embodiment of the present invention consists of that (a) spores of *Bacillus subtilis* are suspended in a carrier solution, are applied onto a plastic sheet or glass surface, and especially onto a polyester sheet to obtain a gel, and are dried, (b) selected first areas of the microorganism coating are optionally exposed to a defined dose of radiation, if so desired by using a series of neutral filters, (c) said first areas optionally exposed to radiation of the microorganism coating are covered, (d) subsequently further selected second areas of the microorganism coating are exposed to the radiation to be detected,
(e) the sheet substrate and the microorganism coating are incubated in a sterile bacterial medium to form proteins, and
(f) the protein formed is selectively stained with a dye and the absorbance of the areas exposed to radiation is photometrically determined.

The above-mentioned embodiment is by no means limited to the specified microorganism. Also in accordance with this embodiment, any radiation-sensitive microorganism may be employed.

The present invention further relates to a device for the detection of radiation by microorganisms. The device thus designated consists of a sheet substrate and a microorganism coating present thereon, said microorganism exhibiting some sensitivity to the radiation to be detected.

Thus, in a particularly preferred embodiment of the invention, a plastic sheet, and especially a polyester sheet having a hydrophilic surface, is selected as the sheet substrate.

An indispensable criterion of the microorganism coating is the sensitivity thereof to the radiation to be detected. Meanwhile, the kind of structure of said microorganism coating is of minor importance. However, particularly advantageous results are obtained in the case where the microorganism coating is a monolayer of the microorganism itself. A microorganism coating in the form of a gel comprising the micoorganism suspended therein has proven to be likewise advantageous. Because of the extremely good drying properties of agarose gel, said gel is preferred for use in combination with spores of Bacillus subtilis.

EXAMPLE

The biological grained material (micoorganism coating) was applied onto a commercially available polyester substrate sheet having a hydrophilic surface, a thickness of 250 μm and a size of 12 cm×26 cm. To this end, spores of Bacillus subtilis were suspended in a 0.5% agarose solution of 70° C., and the suspension was applied onto the sheet (20 ml of the suspension containing $5 \times 10^7$ spores per 100 cm² of the sheet surface). After the agarose solution had solidified, the gel was dried at 65° C. over night.

The sheet, for a calibration of various dose-effect curves in response to varied incubation conditions, was provided with calibration series. This was effected by exposing areas of 20 cm×1.6 cm in size and spaced apart 2 cm from the longitudinal edge of the sheet for 20 minutes to the radiation emitted from an artificial source of irradiation having a constant irradiance and spectral composition (sun simulator). The area thus exposed was covered with 10 different neutral filters, the transmission values of which were in the range of from about 100% to 0.4%.

Then, for a biologically weighted quantification of the UV dose, the areas exposed as above were covered, and the sheet was exposed in the open air in suitable exposure containers in a horizontal position. Only predetermined areas in the middle of the sheet were exposed to the sunlight.

After the termination of the exposure to radiation, the sheet was incubated at 34.5° C. in 500 ml of sterile bacterial nutrient medium under slight agitation for 4 hours. In the course thereof, surviving spores germinated and grew to form microcolonies of from 10 to 100 monocellular organisms. The protein was selectively dyed by 60 minutes of staining and 60 minutes of destaining. The staining agent was Coomassie dye. The sheet was dried, cleaned with 100% methanol and once more dried, and the absorbance values of the exposed areas were then measured at $\lambda = 590$ nm.

The following Table shows the resulting proportions of biologically weighted UV light in various radiation sources.

In addition to quantifying the sunlight, a PHILIPS Home Sun and a 1,000 Watt Xenon Lamp with special filter for a simulation of sunlight were measured in the respective distances.

TABLE

| Proportion of biological weighted UV light* in various sources of radiation. | | | | | |
|---|---|---|---|---|---|
| | UV-C ← | Wave Length Range [nm] UV-B | | UV-A → | Distance Sheet to Source of |
| | <280 | 280–293 | 293–312 | 312–328 | >328 | Radiation |
| Sun; Cologne; July, 2 p.m.–3 p.m. | *0 | 0.2 | 1.2 | 1.2 | 4 | |
| PHILIPS Home Sun | 0 | 1.2 | 2.8 | 2 | 6.4 | 30 cm |
| 1,000 W Xenon with Special filter for sunlight simulation | 9.2 | 1.2 | 8.8 | 1.2 | 2 | 40 cm |
| Laboratory sunlight simulation box | 30 | 7 | 9 | 1 | 7 | 30 cm |

*Data in relative units per hour

I claim:
1. A method for the biological detection of radiation using microorganisms, comprising the sequential steps of:
   (a) providing a sheet substrate onto which microorganisms have been applied as a coating and dried to form a dry film,
   (b) exposing selected test areas of the microorganism coating to the radiation to be detected,
   (c) while maintaining said coating as a dry film, initiating microbial biosynthesis in the areas of the microorganism coating upon termination of the exposure to radiation, and
   (d) while maintaining said coating as a dry film, photometrically determining the formation of at least one product of the microbial biosynthesis in the areas of the microorganism coating exposed to the radiation to be detected, without removing said coating from said substrate.

2. The method according to claim 1 characterized in that selected control areas of the microorganism coating are first exposed to a defined dose of radiation and are then protected from further incident radiation, including the radiation to be detected, prior to the exposing step (b).

3. The method according to claim 1, characterized in that the product of microbial biosynthesis determined in step (d) is a product resulting from microorganism inactivation or growth inhibition, or both.

4. The method according to claim 1, characterized in that edge-type filters are used for selecting the wave length ranges of the radiation to be detected.

5. The method according to claim 1 characterized in that the radiation to be detected is X-ray radiation or ultraviolet radiation.

6. The method of claim 5 characterized in that the radiation to be detected is in the UV-A-B-or-C- range.

7. The method according to claim 1 characterized in that said coating is applied as a suspension to form a gel for containing spores, after which said gel is dried to form said dry film.

8. The method according to of claim 1 characterized in that the survival rate and/or the mutation frequency of the microorganism in the areas exposed to the radiation is measured.

9. The method according to claim 2 characterized in that a polyester sheet is provided as said substrate onto which spores of Bacillus subtilis, suspended in a carrier solution, have been applied, to form a gel which is dried to form said dry film, said defined dose of radiation is selectively provided by using a series of neutral filters, (c) said control areas exposed to radiation of the microorganism are covered, said microbial biosynthesis is initiated by incubating the sheet substrate dry film after termination of exposure to the radiation to be detected in a sterile bacterial medium to form at least one protein, product and the at least one product protein formed is selectively stained with a dye prior to the photometrically determining step.

* * * * *

UNITED STATES PATENT AND TRADEMARK OFFICE
CERTIFICATE OF CORRECTION

PATENT NO. : 5,371,004
DATED : December 6, 1994
INVENTOR(S) : Lothar Quintern

It is certified that error appears in the above-indentified patent and that said Letters Patent is hereby corrected as shown below:

Col. 1, line 60, "Herneck" should be changed to --Horneck--.

Col. 1, line 67, "Fain" should be changed to --main--.

Col. 3, line 66, "sc" should be changed to --so--.

Col. 7, claim 8, line 20, delete "of".

Col. 8, claim 9, line 6, "Bacillus subtilis" should be changed to --*Bacillus subtilis*--.

UNITED STATES PATENT AND TRADEMARK OFFICE
CERTIFICATE OF CORRECTION

PATENT NO. : 5,371,004
DATED : December 6, 1994
INVENTOR(S) : Lother Quintern

It is certified that error appears in the above-indentified patent and that said Letters Patent is hereby corrected as shown below:

Col. 8, claim 9, delete lines 11-12.

Col. 8, claim 9, line 14, after "substrate", insert --and--.

Col. 8, claim 9, line 16, delete the comma.

Col. 8, claim 9, line 17, before "and", insert a comma.

Co. 8, claim 9, line 18, "product protein" should be changed to --protein product--.

Signed and Sealed this

Thirteenth Day of February, 1996

Attest:

BRUCE LEHMAN

*Attesting Officer*  *Commissioner of Patents and Trademarks*